United States Patent [19]
Sifniades et al.

[11] Patent Number: 5,932,724
[45] Date of Patent: Aug. 3, 1999

[54] PROCESS FOR DEPOLYMERIZING NYLON-CONTAINING WASTE TO FORM CAPROLACTAM

[75] Inventors: Stylianos Sifniades, Madison; Alan Bart Levy, Randolph, both of N.J.; Jan Agnes Jozef Hendrix, Born, Netherlands

[73] Assignees: AlliedSignal Inc., Morristown, N.J.; DSM N.V., Netherlands

[21] Appl. No.: 08/843,502

[22] Filed: Apr. 16, 1997

Related U.S. Application Data

[62] Division of application No. 08/569,640, Dec. 8, 1995, Pat. No. 5,681,952.

[51] Int. Cl.$^6$ ................................................. C07D 201/12
[52] U.S. Cl. ................................................................ 540/540
[58] Field of Search ..................................................... 540/540

[56] References Cited

U.S. PATENT DOCUMENTS

| | | | |
|---|---|---|---|
| 2,343,174 | 2/1944 | Edison et al. | 260/78 |
| 2,348,751 | 5/1944 | Peterson | 260/78 |
| 3,182,055 | 5/1965 | Bonfield et al. | 260/239.3 |
| 3,317,519 | 5/1967 | Lazarus et al. | 260/239.3 |
| 3,939,153 | 2/1976 | Fowler | 260/239 |
| 3,988,406 | 10/1976 | Nakamura et al. | 264/68 |
| 4,051,212 | 9/1977 | Grigat et al. | 264/102 |
| 4,107,160 | 8/1978 | Dicoi et al. | 260/239 |
| 4,578,510 | 3/1986 | Doerr | 562/483 |
| 4,605,762 | 8/1986 | Mandoki | 562/483 |
| 4,620,032 | 10/1986 | Doerr | 562/483 |
| 5,169,870 | 12/1992 | Corbin et al. | 521/49.8 |
| 5,233,037 | 8/1993 | Nielinger et al. | 540/540 |
| 5,241,066 | 8/1993 | Davis et al. | 540/540 |
| 5,266,694 | 11/1993 | Moran, Jr. | 540/540 |
| 5,294,707 | 3/1994 | Kotek | 540/540 |
| 5,310,905 | 5/1994 | Moran, Jr. | 540/540 |
| 5,359,062 | 10/1994 | Fuchs et al. | 540/540 |
| 5,360,905 | 11/1994 | Fuchs et al. | 540/540 |
| 5,455,346 | 10/1995 | Kopietz et al. | 540/540 |
| 5,457,197 | 10/1995 | Sifniades et al. | 540/540 |
| 5,466,346 | 11/1995 | Chou et al. | 204/72 |
| 5,468,900 | 11/1995 | Moran, Jr. et al. | 562/590 |
| 5,495,014 | 2/1996 | Fuchs et al. | 540/538 |
| 5,495,015 | 2/1996 | Bassler et al. | 540/540 |
| 5,536,831 | 7/1996 | Kopietz et al. | 540/540 |
| 5,565,590 | 10/1996 | Zima et al. | 554/69 |

FOREIGN PATENT DOCUMENTS

| | | |
|---|---|---|
| 143502 | 11/1971 | Czech Rep. . |
| 608454 | 8/1994 | European Pat. Off. . |
| 627417A1 | 12/1994 | European Pat. Off. . |
| 60-20379 | 5/1985 | Japan . |
| 793598 | 4/1958 | United Kingdom . |
| 1017985 | 1/1966 | United Kingdom . |
| 94/06763 | 3/1994 | WIPO . |

OTHER PUBLICATIONS

L.A. Dmitrieva et al., Fiber Chemistry, vol. 17, No. 4, Mar. 1986, pp. 229–241.

Translation of H. Ludewig et al., "Work–Up of Polyamide (Perlon, Nylon, Trelon) Wastes According to the Depolymerization–Filtration Method", *Faserforshung und Textiletechnik* 5(7), pp. 277–284 (1954).

Chemical Abstracts 49, 9281h (1955).

N.D. Katorzhnov et al., "Effect of Average Molecular Weight of the Polymer on the Rate of Caprolactam Formation during Thermal Depolymerization of Unstabilized Polycaprolactam", *Prikl. Chim.* 32, pp. 655–658 (Aug. 16, 1957).

N.D. Katorzhnov et al., "Reaction Mechanism of the Thermal Depolymerization of Polycaprolactam", *Prikl. Chim.* 32, pp. 1395–1399 (May 8, 1958).

S.Smith, "The Re–Equilibration of Polycaproamide", *Journal of Polymer Science XXX*, pp. 459–478 (1958).

Translation of F. Mikula et al., "Depolymerization of Polycaprolactam Wastes to Monomeric 6–Caprolactam", *Chemicky Prumysl.* 17/42(3), pp. 132–137 (1967).

A.K. Mukherjee et al., "Depolymerization of Poly–ϵ–Caprolactam Catalyzed by Sodium Hydroxide", *Journal of Applied Polymer Science 22*, pp. 361–368 (1978).

Chemical Abstracts 94, 16433y (1980).

Conrad, "New Chemical Methods", *Chemie–Ing. Techn.* 45(24), 1514 (1973).

*Primary Examiner*—Mukund J. Shah
*Assistant Examiner*—Bruce Kifle
*Attorney, Agent, or Firm*—Melanie L. Brown; Virginia S. Andrews; Roger H. Criss

[57] ABSTRACT

The present invention provides an efficient process for the recovery of caprolactam from polycaprolactam-containing waste material. The present process for depolymerizing multi-component waste material comprising polycaprolactam and non-polycaprolactam components to form caprolactam comprises the step of: in the absence of added catalyst, contacting the multi-component waste material with superheated steam at a temperature of about 250° C. to about 400° C. and at a pressure within the range of about 1 atm to about 100 atm and substantially less than the saturated vapor pressure of water at the temperature wherein a caprolactam-containing vapor stream is formed. The formed caprolactam may then be used in the production of engineered resins and fibers.

6 Claims, 1 Drawing Sheet

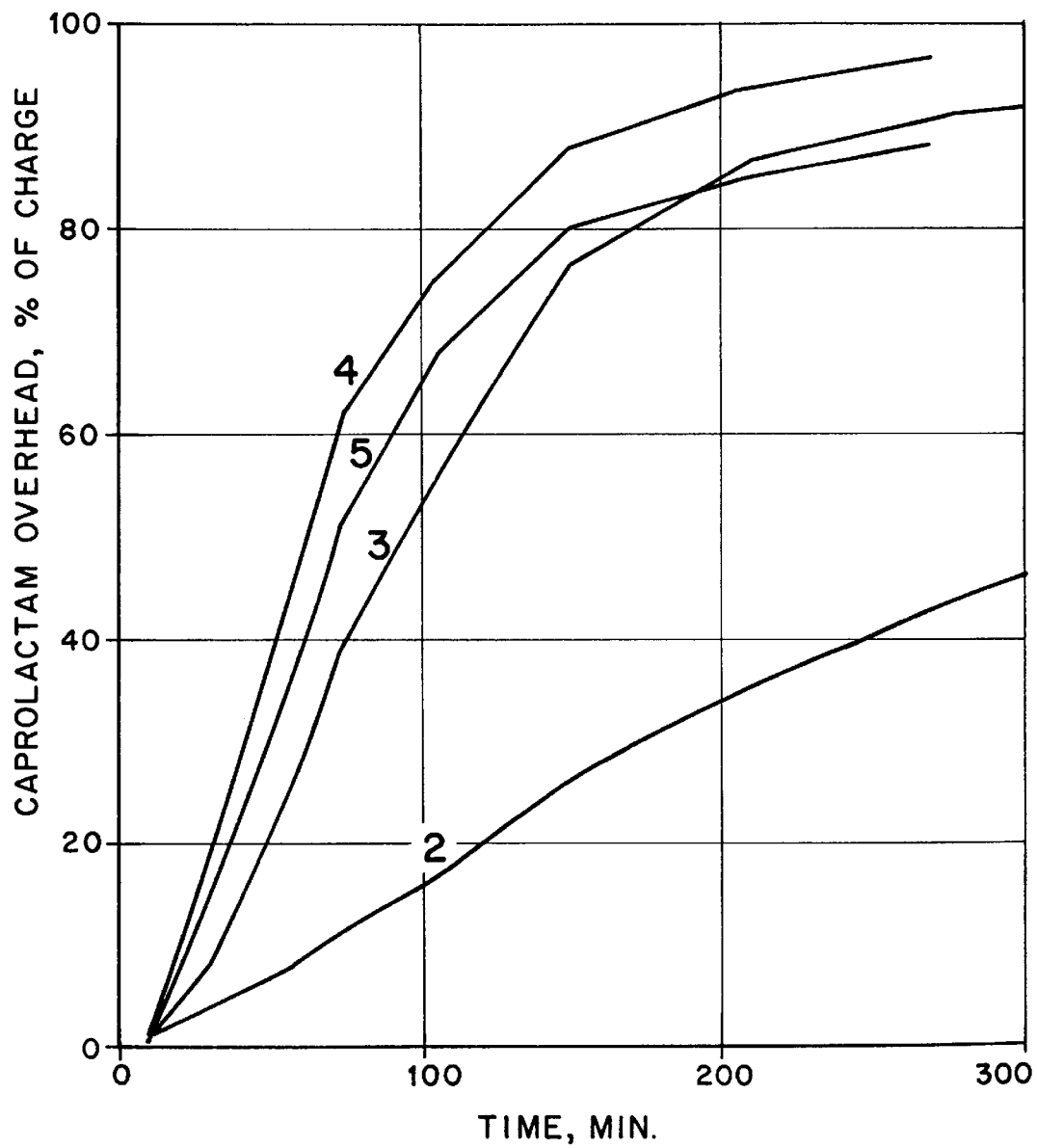

PROCESS FOR DEPOLYMERIZING NYLON-CONTAINING WASTE TO FORM CAPROLACTAM

This application is a division of application Ser. No. 08/569,640, filed Dec. 8, 1995 now U.S. Pat. No. 5,681,952.

BACKGROUND OF THE INVENTION

The present invention relates to a process for the depolymerization of nylon-containing waste to form caprolactam.

Recovery of caprolactam from nylon 6 scrap (in other words, nylon 6 polymer that is substantially free of non-nylon 6 materials) has been practiced for at least twenty years. In general, nylon 6 is depolymerized by heating at elevated temperatures, usually in the presence of a catalyst and/or steam. See U.S. Pat. Nos. 4,107,160; 5,233,037; 5,294,707; 5,359,062; 5,360,905; 5,468,900; and Example 5 of European Patent Application 608,454. The caprolactam produced may be removed as a vapor stream as taught by AlliedSignal's U.S. Pat. No. 3,182,055. An extensive review of the field has been given by L. A. Dmitrieva et al, Fibre Chemistry, Vol. 17, No. 4, March 1986, pp. 229–241. Also, see U.S. Pat. No. 3,939,153.

In contrast to the depolymerization of nylon 6, nylon 66, which is substantially free of non-nylon 66 materials, is depolymerized by hydrolysis as taught by U.S. Pat. Nos. 4,578,510; 4,605,762; and 4,620,032.

U.S. Pat. No. 5,266,694 teaches that a mixture of nylon 6 and nylon 66 may be depolymerized by use of a catalyst. U.S. Pat. No. 5,310,905 teaches that a mixture of nylon 6 and nylon 66 is first separated from consumer waste, e.g. used carpet or carpet scrap, by extraction with aliphatic carboxylic acid; the filtrate comprising the acid and extracted nylon 6 and nylon 66 is then depolymerized. U.S. Pat. No. 5,241,066 teaches that a mixture of nylon 6 and PET, which is acid insoluble, is mixed with acid so that the dissolved nylon 6 may be removed from PET; the removed nylon is then depolymerized. AlliedSignal's U.S. Pat. No. 3,317,519 teaches that a yarn blend of nylon 6 and PET may be depolymerized by heating with aqueous alkali metal hydroxide at elevated pressure.

However, in the case of multi-component mixtures or composites that contain nylon 6 as one component, recovery of caprolactam is complicated by the presence of the other components. These other components and/or their decomposition products generated under conventional nylon 6 depolymerization conditions interfere with the isolation of caprolactam of adequate purity, thus necessitating expensive additional purification steps.

It would be particularly beneficial if an inexpensive method could be developed for the recovery of caprolactam from multi-component composites or materials that include nylon 6, such as carpets. The prospect of recycling such material presents a tremendous opportunity to reduce landfill usage and the costs of disposal, as well as an opportunity to reuse natural resources.

Carpets include a face fiber that is adhered to a backing (support) material which may include jute, polypropylene, latex (such as a styrene-butadiene rubber (SBR)) and a variety of inorganic materials such as calcium carbonate, clay, or hydrated alumina fillers. Nylon 6 is often used for the face fiber. Typically, carpet comprises about 20–55 percent by weight face fiber and 45–80 percent by weight backing materials. In addition, the fiber contains dyes, soil repellents, stabilizers, and other compounds added during fiber and/or carpet manufacture. Waste carpet may also contain a host of other impurities, which will collectively be referred to herein as "dirt".

These non-nylon 6 components interfere with caprolactam recovery. For example, one of the most difficult problems is that alkaline components, such as the calcium carbonate filler, neutralize acidic catalysts, such as phosphoric acid, that are conventionally used to promote nylon 6 depolymerization, thus requiring the use of increased amounts of catalyst. Another problem is that polypropylene and latex partially decompose to a mixture of hydrocarbons that co-distill with caprolactam. The remaining, partially decomposed, non-distilled portion, along with the filler and other inorganic components, renders the reaction mixture very viscous and difficult to process in conventional equipment.

Indicative of the difficulties encountered in attempting to recover caprolactam from nylon 6 carpet are the results described in U.S. Pat. No. 5,169,870 (Corbin et al.) and WO 94/06763 (Corbin et al.). In Example 1 of each publication, the crude yield of caprolactam was reported as 56% from a feedstock obtained by mechanically separating a portion of the carpet backing and subjecting the enriched nylon 6 to depolymerization; steam and 85% phosphoric acid were used in the depolymerization respectively at the rate of 33 and 0.55 parts per part of crude caprolactam produced. In Example 3 of each publication, a carpet was depolymerized without prior mechanical separation of the backing; steam and 85% phosphoric acid were used respectively at the rate of 51 and 0.30 parts per part of crude caprolactam produced. (The yield of caprolactam was not stated.) It is evident that the high expenditure of steam and phosphoric acid, and the low yield of caprolactam, render this process economically unattractive. Examples 4 and 5 of WO 94/06763 report higher yields of caprolactam, but initial separation techniques to reduce the amount of $CaCO_3$ prior to depolymerization were required. U.S. Pat. No. 5,455,346 describes a process applicable to the recovery of caprolactam from mixtures containing nylon 6, including nylon 6 carpets. Initial separation techniques are also used to increase the nylon 6 content of the mixture prior to depolymerization; Example 13 teaches that the carpeting was freed from polyamide-free components until the polycaprolactam was 75 percent by weight based on the mixture. In contrast, it is often desirable to avoid such separation techniques.

One way to circumvent the problems associated with the presence of non-nylon 6 components in a material that includes both nylon 6 and non-nylon 6 components involves heating the waste material under pressure in water, separating the resulting solution from the non-nylon 6 components, and recovering caprolactam from the aqueous solution by further treatment. Processes based on these general principles are described in Czechoslovakian Patent No. 143,502 to Petru et al. and in AlliedSignal's U.S. Pat. No. 5,457,197 to Sifniades et al. Although these processes are an improvement, they suffer from the disadvantage of requiring multiple steps and/or high pressure operations with associated higher capital investment and operating expenses.

A need still exists, therefore, for an efficient process for recovery of caprolactam from multi-component materials that include nylon 6.

SUMMARY OF THE INVENTION

The invention provides another process for depolymerizing multi-component waste material comprising polycaprolactam and non-polycaprolactam components to form caprolactam which avoids the problems associated with the previous recovery methods. The process comprises the step of: in the absence of added catalyst, contacting the multi-component waste material with superheated steam at a temperature of about 250° C. to about 400° C. and at a pressure within the range of about 1 atm to about 100 atm and substantially less than the saturated vapor pressure of water at the temperature wherein a caprolactam-containing vapor stream is formed.

Optionally, the multi-component waste material is contacted for a short time period with liquid water under elevated temperatures and pressures prior to contacting with steam as discussed above.

According to preferred embodiments, the multi-component waste material is nylon 6 carpet.

BRIEF DESCRIPTION OF THE DRAWING

The invention will be described in more detail below with reference to drawing, wherein FIG. 1 is a graph illustrating one advantage of the invention.

DETAILED DESCRIPTION OF THE PREFERRED EMBODIMENTS

As used herein, "multi-component, nylon 6 waste material" denotes material or articles that include nylon 6 and at least one other component which may be a non-hydrolyzable polymer, an inorganic or organic material, or other types of materials, and that has been, is intended to be, or otherwise would have been discarded by a consumer, manufacturer, distributor, retailer, installer and the like. The other components can constitute from about 5 to about 95, preferably about 20 to about 80 weight percent of the multi-component, nylon 6 waste material. "Multi-component, nylon 6 waste material" does not include waste material composed solely of scrap nylon 6 polymeric and/or oligomeric material, such as material generated during the production of intermediate articles such as fiber, chip, film or molded articles which intermediate articles are then incorporated or transformed into end use multi-component products such as carpets and packaging. Examples of such scrap material are yarn waste, chip waste, or extruder slag.

The multi-component nylon 6 waste material comprises up to a total of about 10 percent by weight with respect to polycaprolactam of at least one of polyhexamethylene adipamide (hereinafter "nylon 66") and polyethylene terephthalate (hereinafter "PET"). Thus, the multi-component nylon 6 waste material may comprise up to a total of about 10 percent by weight with respect to polycaprolactam of nylon 66, PET, or a mixture of nylon 66 and PET. For purposes of convenience, "multi-component, nylon 6 waste material" may be referred to as "multi-component waste material" hereafter. The foregoing weight percentages exclude the presence of dirt, a previously defined term.

A preferred embodiment is the recovery of caprolactam from waste carpet material that includes nylon 6 face fiber and non-nylon 6 components.

As used herein, "fiber" denotes an elongated body, the length dimension of which is much greater than the transverse dimensions of width and thickness. Accordingly, "fiber" includes, for example, monofilament, multifilament yarn (continuous or staple), ribbon, strip, staple and other forms of chopped, cut or discontinuous fiber, and the like having regular or irregular cross-sections. "Fiber" includes a plurality of any one of the above or a combination of the above.

As used herein, "carpet material" denotes carpet which has not been subjected to any mechanical separation (referred to herein as "whole carpet"), as well as any mixture of carpet components that is a product of separation, mechanical or otherwise, of whole carpet (referred to herein as "beneficiated carpet"). "Waste carpet material" denotes carpet material that has been, is intended to be, or otherwise would have been discarded by a consumer, manufacturer, distributor, retailer, installer and the like.

According to the process of the current invention, caprolactam is formed by contacting the multi-component waste material with superheated steam at elevated temperatures and atmospheric or higher pressures and removing a vapor stream containing caprolactam from the contact region. The term "superheated steam" as used herein means steam that is heated to a temperature substantially higher than the temperature at which condensation to liquid water would take place at the pressure used to convey said steam. An important benefit of the process is that no catalyst is needed for recovering caprolactam from whole carpet waste. Whole carpet generally includes calcium carbonate, which can neutralize an acidic catalyst.

Accordingly, for depolymerization processes employing an acidic catalyst, such as phosphoric acid, increased amounts of catalyst are required to effect depolymerization, thereby rendering the process impractical or uneconomical. Accordingly, for the present process, no acidic catalyst is added to the vessel in which the multi-component, nylon 6 waste material is contacted with superheated steam. It should be understood, however, that the waste material feedstock may include minor amounts of materials (for example, contaminants) that incidentally are recognized in the art as catalysts. However, the subject process does not rely on the presence or addition of any such catalytic materials in the vessel.

A further benefit is that even a feedstock composed substantially of whole carpet can be employed in the process, with sufficient yields of caprolactam. This avoids the need for separation processes, to remove various components in carpet, prior to depolymerization.

When nylon 66, PET, or a mixture of nylon 66 and PET is present in the multi-component waste material in an amount of up to a total of 10 percent by weight with respect to nylon 6, these polymers do not interfere with the present depolymerization process or subsequent purification procedures involving distillation of caprolactam. This is an added advantage of the present process, because in carpet recycling, it is virtually certain that small quantities of nylon 66 and PET carpet will find their way in the nylon 6 carpet feedstock. In contrast, in nylon 6 depolymerization processes that rely on liquid phase depolymerization (see U.S. Pat. Nos. 5,359,062 and 5,455,346), the caprolactam produced in solution is sensitive to polymerization initiated by the adipic and terephthalic acids produced by hydrolysis of said polymers. Therefore, such processes must employ low temperature methods, such as extraction, for caprolactam purification, or they must be coupled with post-depolymerization procedures, such as in AlliedSignal's U.S. Pat. No. 5,457,197 to Sifniades et al.

The multi-component waste material is preferably fed to the reactor as a melt. This feeding may be achieved by using an extruder, gear pump, or other means known in the art. Some feeding systems, such as extruders, allow the development of relatively high pressures in the melt. This offers the option of contacting the melt with liquid water at elevated temperatures for a short period of time at little added cost. This may be achieved, for example, by introducing water under pressure in the extruder barrel. The contact time between the melt and water may be extended by placing a high pressure pipe between the extruder exit and reactor. In this optional pretreatment step, the multicomponent waste material is combined with liquid water and heated at a sufficient temperature for a time period sufficient to effect an initial depolymerization of the polycaprolactam. The depolymerization products formed in this step may include reduced molecular weight polycaprolactam, caprolactam, caprolactam linear oligomers, and caprolactam cyclic oligomers. Such contact accelerates caprolactam production in subsequent process steps as disclosed in AlliedSignal's U.S. Pat. No. 5,457,197 to Sifniades et al. The disclosure of AlliedSignal's U.S. Pat. No. 5,457,197 is incorporated herein by reference.

For the recovery of caprolactam to be economical, it is desirable to utilize as inexpensive equipment and as little steam as technically feasible. A good index of the economy of the process is the concentration of caprolactam obtained in the overheads, which bears an inverse relationships to the amount of steam used. Concentrations in excess of 15 wt. % can be obtained by appropriate design of the reactor and choice of operating conditions as described below.

The reaction temperature should be at least about 250° C. but not higher than about 400° C. Generally, the rate of caprolactam formation increases with increasing temperature. However, the rate of side reactions of nylon 6 such as evolution of ammonia also increases with temperature and so does the rate of reactions of the non-nylon 6 components of the multi-component material.

Temperatures of at least about 250° C. are preferred because below 250° C., caprolactam formation may be too slow. Temperatures no greater than about 400° C. are preferred, as above 400° C. side reactions of nylon 6 and reactions of the non-nylon 6 components may become prohibitively fast. A preferred temperature range is about 280° C. to about 350° C., more preferably a temperature in the range of about 300° C. to about 340° C.

The pressure should be at least atmospheric but higher pressures offer certain advantages as will be explained below. Other factors, such as the availability and operating cost of high pressure equipment may influence the choice of pressure.

Regarding the effect of pressure, it has been found that for a given temperature and steam flow, increasing the reactor pressure generally increases the caprolactam concentration in the overheads up to an optimal pressure. Further small increases in pressure have little effect on caprolactam concentration. However, a large increase in pressure beyond the optimal pressure results in decreased caprolactam concentration. Generally, the higher the operating temperature, the higher is the optimal pressure at which maximum caprolactam concentration is obtained. For example at about 320° C. and a steam flow of 1 reaction mass per hour, the optimal pressure is about 11 atm (about 1114 kPa); at about 340° C. and a steam flow of 2.0 reaction mass per hour, the optimal pressure is about 15 atm (about 1520 kPa). Optimal pressure conditions under different operating conditions within the scope of this invention can be determined by those skilled in the art.

It will be appreciated that the optimal pressure is well below the saturated vapor pressure of water at the operating temperature. For example, the saturated vapor pressure of water is 111 atm at 320° C., and 144 atm at 340° C. Therefore, it is clear that in the current process, no liquid aqueous phase is present.

The effect of pressure on caprolactam concentration at constant steam flow is matched by its effect on the rate of production of caprolactam. Therefore, operating near the optimal pressure minimizes not only steam usage but also reactor volume.

A further benefit of operating close to the optimal pressure is the suppression of side reactions leading to ammonia formation. We have found that at a given temperature, ammonia production during polycaprolactam depolymerization is lower the faster caprolactam is removed from the reaction zone.

Although not wishing to be bound by any theory, it is surmised that as pressure increases at a given temperature and steam flow, the amount of water that dissolves in nylon 6 is increased resulting in the acceleration of depolymerization reactions. It will be appreciated that the action of water in the depolymerization of nylon 6 to caprolactam is catalytic, that is, no net amount of water is consumed in the overall conversion of nylon 6 to caprolactam. Caprolactam is generally formed by cleavage of caprolactam molecules from the ends of the nylon 6 chain, in a reversal of the polyaddition reaction which constitutes caprolactam polymerization. Water promotes caprolactam formation by virtue of promoting the cleavage of amide bonds, which results in the formation of more end groups. Water is consumed only to the extent that some of the nylon 6 charged is not converted to caprolactam. As caprolactam is produced at a faster rate, its partial pressure in the vapor phase increases. However, the partial pressure of water also increases, approximately in proportion to the applied pressure. The caprolactam/water ratio in the overheads is proportional to the ratio of the corresponding vapor pressures.

Therefore, increasing the reactor pressure can result in an increase or a decrease of caprolactam concentration in the overheads, depending on whether the caprolactam vapor pressure increases faster or slower than the water vapor pressure. Evidently, at pressures below the optimal pressure, the caprolactam partial pressure increases faster than the partial pressure of water as the reactor pressure is increased. At pressures above the optimal pressure, the partial pressure of water increases faster than the partial pressure of caprolactam as the reactor pressure is increased.

A secondary effect of pressure is the suppression of caprolactam cyclic dimer. The dimer is formed reversibly along with caprolactam during nylon 6 depolymerization. When the depolymerization is carried out at atmospheric pressure, relatively large amounts of the dimer are found in the overheads, as much as 3–4 wt % of the caprolactam. Increasing the pressure decreases the ratio of dimer to caprolactam in the overheads. Since dimer formation is reversible, dimer that does not distill over is converted eventually to caprolactam. Suppressing dimer concentration in the overheads is beneficial not only from the point of view of product yield, but also because the dimer, when present at high concentrations, may be deposited as a solid and clog the transfer lines and the condenser.

In view of these findings, the operating pressure should range from about 1 atm up to about 100 atm (about 101 kPa to about 10130 kPa). However, the pressure should be substantally less than the saturation vapor pressure of water under the operating temperature to ensure that liquid water does not condense in the reactor. For example, at 300° C., the saturated vapor pressure of water is 85 atm. Operation at that temperature should be carried out at pressures ranging from about 1 atm to about 75 atm. For the preferred temperature range of about 280° C. to about 350° C., the preferred pressure range is about 1 atm to about 30 atm (about 101 kPa to about 3940 kPa). For the more preferred temperature range of about 290° C. to about 340° C., the preferred pressure range is about 3 atm to about 15 atm (about 304 kPa to about 1520 kPa). The rate of steam flow should be sufficient to remove caprolactam from the reactor, but not so high as to cause undue dilution of caprolactam in the overheads. Since a high caprolactam concentration in the overheads is desired, the steam flow should be proportional to the rate of production of caprolactam, which is generally proportional to the mass of nylon 6 charged and also increases with temperature.

The contact of the multi-component waste material with steam is effected in a vessel designed to withstand the requisite temperature and pressure, as well as the corrosiveness of the reactants. Since no corrosive catalysts, such as acids, are required in this process, no special alloys are required, and a stainless steel vessel is adequate.

Good contact between steam and the multi-component waste material is essential for an effective operation. Such contact may be achieved by various means known generally in the art. As an example, steam may be sparged through the material using a multiplicity of inlets, for example, using a steam distributor. Improved contact may be achieved by including mechanical agitation in the reactor, for example, using a combination of rotating paddles and static fins.

The process of the current invention may be carried out either continuously or in batch fashion. In the latter case, the multi-component waste material is charged to the reactor all at once and steam is sparged continuously until most of the caprolactam has been recovered. Generally, in the batch process, caprolactam concentration in the overheads diminishes as the charge is depleted of nylon 6. Said concentration may be maintained at relatively high levels throughout the process by gradually increasing the temperature and/or decreasing the steam flow as the run process.

In a continuous process, both the multi-component waste material and the steam are fed continuously to the reactor. Caprolactam is recovered overhead, while a nylon 6 depleted melt is discharged from the bottoms. To maintain a high caprolactam concentration in the overheads, it is desirable to run the steam countercurrent to the melt flow. This can be achieved by using a series of continuous stirred reactors (CSTRs) in which melt flows from the first reactor to the last while steam flows in the opposite direction. However, it is also possible to operate with steam crossflow or crosscurrent flow. In this mode, the melt flows from the first reactor to the last, whereas fresh steam is supplied to each reactor. If desired, the steam flow to each reactor may diminish as the nylon content of the melt diminishes. Although crossflow may generally result in higher overall consumption of steam, it is simpler to implement and may require lower capital investment.

In a preferred embodiment of the process, nylon 6 carpet melt is fed at the top of a continuous flow reactor. Superheated steam is fed through a distributor at the bottom of the reactor countercurrent to the flow of the melt. A vapor stream containing caprolactam is collected at the top of the reactor and nylon 6 depleted melt exits at the bottom. The carpet may be fed by means of an extruder, gear pump, or other device. The reactor may be divided into several stages by means of baffles. Means may be provided for mechanical agitation in each stage. Heat is provided to the reactor mainly by means of the superheated steam. Additional heat may also be provided through the carpet feed, especially if an extruder is used to feed the carpet, and through the wall of the reactor.

Caprolactam may be separated from other components of the distillate. The vapors from the reactor overhead may be sent to a partial condenser to obtain a condensate containing caprolactam. Fiber grade caprolactam may be obtained from this condensate by further purification including distillation, crystallization and other conventional techniques known in the art. For example, the caprolactam purification process of AlliedSignal's U.S. Pat. Nos. 2,813,858; 3,406,176 or 4,767,503 to Crescentini et al. may be used.

The purified caprolactam may then be used to make polycaprolactam using a known process such as disclosed in AlliedSignal's U.S. Pat. Nos. 3,294,756; 3,558,567; or 3,579,483. The polycaprolactam may then be used in known engineered materials such as disclosed in AlliedSignal's U.S. Pat. Nos. 4,160,790; 4,902,749; or 5,162,440 or spun into fiber using a known process such as disclosed in AlliedSignal's U.S. Pat. Nos. 3,489,832; 3,517,412; or 3,619,452.

The following examples illustrate various preferred embodiments of the invention.

EXAMPLE 1

Whole carpet feedstock containing 57.6% by weight nylon 6 was prepared by extruding a shredded carpet having nylon 6 face fiber and backing of polypropylene and calcium-filled SBR and grinding the extrudate to 5 mesh chips. A 178.8 g portion of the feedstock was placed in a cylindrical stainless steel reactor of 24.5 mm diameter and 1070 mm height. The reactor was connected to a condenser equipped with a back-pressure valve at the exit set at 9.2 atm (932 kPa). Superheated steam was blown through the bottom of the reactor at the rate of 3 g/min while the temperature of the reactor was maintained at 300° C.. Overheads cuts were taken periodically and analyzed for caprolactam, caprolactam oligomers, and ammonia. The concentration of caprolactam reached 15 wt. % by the third cut and gradually declined to 3.8 wt. % as the nylon content of the carpet was depleted. Overall, 1094 g of distillate were collected within 6.0 hours containing 92.5 g caprolactam, 0.54 g caprolactam cyclic dimer, and 0.126 g ammonia. The molar yield of caprolactam based on nylon 6 present in the carpet charged was 89.8%. The moles of cyclic dimer (expressed as caprolactam equivalents) and moles of ammonia relative to lactam produced were 0.58% and 0.91% respectively.

EXAMPLES 2–7

Several more examples were carried out using the same feedstock and apparatus as in Example 1. In all cases, the charge was 180±2 g. The results are summarized in Table 1 below. It is seen that increasing the temperature at essentially constant pressure and steam rate, the maximum concentration of caprolactam in the overheads increases (Examples 1 and 4); increasing the pressure at constant temperature and steam rate increases the caprolactam concentration until an optimal level of pressure is reached, and decreases the yield of caprolactam cyclic dimer (Examples 2–5); and increasing the steam rate at constant temperature and pressure decreases the caprolactam concentration but increases the caprolactam yield (Examples 4 and 6). Example 7 shows that high caprolactam concentration can be achieved at increased steam flow by simultaneously increasing the temperature and pressure.

The effect of pressure on the rate of caprolactam production is demonstrated in FIG. 1, in which the cumulative amount of caprolactam in the overheads is plotted as a function of time for Examples 2–5, in which the temperature and the steam flow were held constant at 320° C. and 3 g/min respectively. The curves are labeled by the number of the Example to which they refer. It is seen that as the pressure is increased from atmospheric (Example 2) to 6.1 atm (Example 3), the rate increases by more than a factor of two. Further increase in pressure to 10.9 atm (Example 4) produces a smaller increase in rate. Further increasing the pressure to 14.9 atm (Example 5) results in a small decrease in rate, indicating that the optimal pressure under these conditions of temperature and steam flow is in the range of 11 to 15 atm. Additionally, comparing FIG. 1 to Table 1, it is apparent that the ammonia to caprolactam ratio bears an inverse relationship to the rate of caprolactam production. Therefore, operating close to the optimal pressure minimizes both dimer and ammonia production relative to caprolactam.

nylon 6 present in the carpet were charged to the autoclave along with the carpet. The rate and selectivity of the depolymerization paralleled that of Example 8. Fractional distillation of the collected overheads produced a fraction containing over 99% caprolactam, and less than 10% of the available caprolactam remained in the distillation bottoms.

EXAMPLE 11

The procedure of Example 10 was repeated, except that polyethylene terephthalate chips were substituted for the nylon 66 chips. Comparable results to Example 10 were obtained.

Comparative Example A

One part of a mixture of nylon 6 and nylon 66 chips in the weight ratio 95:5 and 6.67 parts of water were placed in a

TABLE 1

STEAM DEPOLYMERIZATION OF NYLON 6 CARPET

| Ex. | Temp. deg C. | Press. atm | Steam g/min | Time min | Maximum Concn % | (a) Caprol. | (b) Dimer | (c) Ammonia |
|---|---|---|---|---|---|---|---|---|
| 1 | 300 | 9.2 | 3 | 360 | 15.0 | 89.8 | 0.58 | 0.91 |
| 2(d) | 320 | 1.0 | 3 | 360 | 5.5 | 48.1 | 2.26 | 5.03 |
| 3 | 320 | 6.1 | 3 | 360 | 18.2 | 91.6 | 0.82 | 1.97 |
| 4 | 320 | 10.9 | 3 | 300 | 23.4 | 90.0 | 0.53 | 1.67 |
| 5 | 320 | 14.6 | 3 | 300 | 22.0 | 87.2 | 0.45 | 2.29 |
| 6 | 320 | 10.9 | 6 | 300 | 14.5 | 95.4 | 0.68 | 1.26 |
| 7 | 340 | 14.6 | 6 | 180 | 24.2 | 93.1 | 0.58 | 2.15 |

(a) Caprolactam overhead, mol % of nylon 6 charged.
(b) Dimer overhead, mol % of caprolactam overhead.
(c) Ammonia overhead, mol % of caprolactam overhead.
(d) The run for Example 2 was discontinued after 360 minutes; caprolactam was produced at a low rate and the ratio of dimer and ammonia to caprolactam was higher than in the other runs.

EXAMPLE 8

A carpet having nylon 6 face fiber and backing of polypropylene and calcium-filled SBR contained about 52% by weight nylon 6. The carpet was cut to strips and about 850 g thereof were charged to a 2 liter stirred autoclave via an extruder. Superheated steam was sparged at the bottom of the autoclave at the rate of 20 g/min while a vapor stream containing caprolactam flowed overhead and was fed to a partial condenser. A condensate containing up to 80% by weight caprolactam was collected. The temperature and the pressure in the autoclave were maintained at 312° C. and 9.2 atm respectively during the run. After one hour of operation, the yield of caprolactam in the collected overheads was about 50% by weight of the nylon charged. At the end of three hours, the yield was over 90% based on the nylon 6 in the starting material. The condensate was filtered through filter-aid to remove a small amount of oils and suspended waxes and submitted to fractional distillation under vacuum. A fraction containing over 99% caprolactam was obtained. Less than 10% of the available caprolactam remained in the distillation bottoms. The distilled caprolactam was further purified via crystallization from water to yield fiber quality caprolactam.

EXAMPLE 9

The caprolactam from Example 8 is spun into fiber using a known spinning process.

EXAMPLE 10

The procedure of Example 8 was repeated, except that nylon 66 chips corresponding to about 5% by weight to the sealed autoclave and heated under autogenous pressure to 300° C. for one hour. Analysis of the resulting solution revealed that about 75% of nylon 6 had been converted to caprolactam. Because caprolactam polymerizes with the mixture of nylon 6 oligomers and nylon 66 oligomers, only a small portion of the caprolactam can be recovered.

Comparative Example B

The procedure of Comparative Example A was repeated, except that polyethylene terephthalate chips were substituted for the nylon 66 chips. Comparable results to Comparative Example A were obtained.

EXAMPLE 12

For a continuous process, the apparatus comprises at least three reactors equipped with inlet at the top and outlet at the bottom for liquid flow, and inlet at the bottom and outlet at the top for vapor flow. The three reactors are connected in series so that liquid flow runs in one direction while vapor flow runs in the opposite direction. Each reactor is equipped with a mechanical agitator and baffles that ensure intimate mixing between liquid and vapor. Waste carpet containing about 50% nylon 6 is shredded and fed to an extruder. The extrudate is continuously fed to the first reactor and exits from the last. Superheated steam is fed to the last reactor at a rate approximately 3 times the extrudate flow and exits from the first reactor. The reactors are held at about 330° C. and 12 atm. The overall residence time of the melt in the reactors is about 4 hours. The exit vapors are sent to a partial condenser where a condensate containing about 90% caprolactam is obtained. Fiber grade caprolactam may be obtained from this condensate by further purification including filtration, distillation, crystallization and other conventional techniques known in the art. A portion of the remaining vapor is purged while the rest is mixed with makeup steam, sent to a superheater, and recycled through the process.

EXAMPLE 13

The caprolactam from Example 12 is used to make an engineered plastic.

From the foregoing description, one skilled in the art can easily ascertain the essential characteristics of this invention, and without departing from the spirit and scope thereof, can make various changes and modifications of the invention to adapt it to various usage's and conditions.

We claim:

1. A process for making polycaprolactam from multi-component polycaprolactam-containing waste non-beneficiated carpet comprising the steps of:
   (a) in the absence of added catalyst, contacting said multi-component polycaprolactam-containing waste non-beneficiated carpet comprising polycaprolactam and non-polycaprolactam components with superheated steam at a temperature of about 250° C. to about 400° C. and at a pressure within the range of about 1 atm to about 100 atm and substantially less than the saturated vapor pressure of water at said temperature wherein a caprolactam-containing vapor stream is formed;
   (b) removing said formed caprolactam-containing vapor stream from said contact region;
   (c) separating said caprolactam from said removed caprolactam-containing vapor stream by partial condensation;
   (d) purifying said separated caprolactam; and
   (e) polymerizing said purified caprolactam.

2. The process of claim 1 which additionally comprises:
   (f) making fiber from said polycaprolactam resulting from step (e).

3. A process for making polycaprolactam from multi-component polycaprolactam-containing waste non-beneficiated carpet comprising the steps of:
   (a) in the absence of added catalyst, contacting said multi-component polycaprolactam-containing waste non-beneficiated carpet comprising polycaprolactam and non-polycaprolactam components countercurrently or crosscurrently with superheated steam in a series of continuous flow stirred reactors at a temperature of about 250° C. to about 400° C. and at a pressure within the range of about 1 atm to about 100 atm and substantially less than the saturated vapor pressure of water at said temperature wherein a caprolactam-containing vapor stream is formed;
   (b) removing said formed caprolactam-containing vapor stream from said contact region;
   (c) separating said caprolactam from said removed caprolactam-containing vapor stream by partial condensation;
   (d) purifying said separated caprolactam; and
   (e) polymerizing said purified caprolactam.

4. The process of claim 3 which additionally comprises:
   (f) making fiber from said polycaprolactam resulting from step (e).

5. A process for making polycaprolactam from multi-component polycaprolactam-containing waste non-beneficiated carpet comprising the steps of:
   (a) in the absence of added catalyst, contacting said multi-component polycaprolactam-containing waste non-beneficiated carpet comprising polycaprolactam and non-polycaprolactam components countercurrently with superheated steam in a vertical tubular reactor at a temperature of about 250° C. to about 400° C. and at a pressure within the range of about 1 atm to about 100 atm and substantially less than the saturated vapor pressure of water at said temperature wherein a caprolactam-containing vapor stream is formed;
   (b) removing said formed caprolactam-containing vapor stream from said contact region;
   (c) separating said caprolactam from said removed caprolactam-containing vapor stream by partial condensation;
   (d) purifying said separated caprolactam; and
   (e) polymerizing said purified caprolactam.

6. The process of claim 5 which additionally comprises:
   (f) making fiber from said polycaprolactam resulting from step (e).

* * * * *